United States Patent
Burtscher (10) Patent No.: US 10,092,965 B2
(45) Date of Patent: Oct. 9, 2018

(54) INDEXABLE CUTTING INSERT AND MILLING TOOL

(71) Applicant: CERATIZIT AUSTRIA GESELLSCHAFT M.B.H., Reutte (AT)

(72) Inventor: Peter Burtscher, Haeselgehr (AT)

(73) Assignee: Ceratizit Austria Gesellschaft m.b.H., Reutte (AT)

( * ) Notice: Subject to any disclaimer, the term of this patent is extended or adjusted under 35 U.S.C. 154(b) by 209 days.

(21) Appl. No.: 15/120,283

(22) PCT Filed: Feb. 19, 2015

(86) PCT No.: PCT/AT2015/000027
§ 371 (c)(1),
(2) Date: Aug. 19, 2016

(87) PCT Pub. No.: WO2015/123708
PCT Pub. Date: Aug. 27, 2015

(65) Prior Publication Data
US 2017/0066065 A1    Mar. 9, 2017

(30) Foreign Application Priority Data
Feb. 20, 2014 (AT) ................ GM75/2014

(51) Int. Cl.
*B23C 5/20* (2006.01)
*A61K 31/4741* (2006.01)
(Continued)

(52) U.S. Cl.
CPC .......... *B23C 5/207* (2013.01); *A61K 31/4741* (2013.01); *A61K 36/66* (2013.01);
(Continued)

(58) Field of Classification Search
CPC ........... B23C 5/20; B23C 5/202; B23C 5/203; B23C 5/207; B23C 2200/12;
(Continued)

(56) References Cited

U.S. PATENT DOCUMENTS

| 4,294,565 A | 10/1981 | Erkfritz |
| 5,443,334 A | 8/1995 | Pantzar |

(Continued)

FOREIGN PATENT DOCUMENTS

| CN | 1116834 A | 2/1996 |
| CN | 103521824 A | 1/2014 |

(Continued)

*Primary Examiner* — Will Fridie, Jr.
(74) *Attorney, Agent, or Firm* — Laurence A. Greenberg; Werner H. Stemer; Ralph E. Locher (57) ABSTRACT

An indexable cutting insert for face milling with high feed rates has: an upper side, a lower side with a smaller outer circumference than the upper side, and side surfaces connecting the upper and lower sides. Rounded cutting corners are formed at the transition between the side surfaces and the upper side. The cutting corners are connected via convexly arched cutting edges, each running convexly curved from one cutting corner to an adjacent cutting corner. Adjacent the cutting edges, the side surfaces have main flanks extending along the respective cutting edge in a continuously convexly curved manner from one cutting corner to an adjacent cutting corner. The main flanks extend in the direction of the lower side only over part of the height of the side surfaces and merge in a stepped manner into secondary surfaces which are set back inward.

16 Claims, 5 Drawing Sheets

(51) Int. Cl.
*B23C 5/06* (2006.01)
*A61K 36/66* (2006.01)

(52) U.S. Cl.
CPC ........ *B23C 5/06* (2013.01); *B23C 2200/0461* (2013.01); *B23C 2200/123* (2013.01); *B23C 2200/125* (2013.01); *B23C 2200/128* (2013.01); *B23C 2200/203* (2013.01); *B23C 2200/243* (2013.01); *B23C 2220/44* (2013.01)

(58) Field of Classification Search
CPC ........ B23C 2200/126; B23C 2200/128; B23C 2200/125; B23C 2200/0461; B23C 2200/123; B23C 2200/203; B23C 2200/243
See application file for complete search history.

(56) References Cited

U.S. PATENT DOCUMENTS

| | | | | |
|---|---|---|---|---|
| 5,720,583 | A * | 2/1998 | Bohnet | ............ B23C 5/202 407/113 |
| 7,040,844 | B1 | 5/2006 | Daiguji | |
| 8,740,509 | B2 * | 6/2014 | Luik | ............ B23C 5/109 407/113 |
| 8,974,156 | B2 * | 3/2015 | Burtscher | ............ B23C 5/202 407/113 |
| 9,144,848 | B2 * | 9/2015 | Konta | ............ B23C 5/109 407/113 |
| 9,475,135 | B2 | 10/2016 | Wandebaeck et al. | |
| 9,555,489 | B2 | 1/2017 | Takahashi | |
| 2006/0210364 | A1 | 9/2006 | Bellmann et al. | |
| 2010/0202839 | A1 | 8/2010 | Fang et al. | |
| 2010/0303563 | A1 * | 12/2010 | Fang | ............ B23C 5/109 407/113 |
| 2013/0115021 | A1 | 5/2013 | Festeau et al. | |
| 2013/0302099 | A1 * | 11/2013 | Choi | ............ B23C 5/08 407/113 |

FOREIGN PATENT DOCUMENTS

| | | |
|---|---|---|
| DE | 102009035754 A1 | 1/2011 |
| EP | 0035848 A2 | 9/1981 |
| EP | 1584390 A2 | 10/2005 |
| JP | S52103081 A | 8/1977 |
| JP | 2002178210 A | 6/2002 |
| JP | 2005169511 A | 6/2005 |
| JP | 2007515303 A | 6/2007 |
| JP | 2013520323 A | 6/2013 |
| WO | 2005065874 A1 | 7/2005 |
| WO | 2011103609 A1 | 9/2011 |
| WO | 2013088851 A1 | 6/2013 |

* cited by examiner

INDEXABLE CUTTING INSERT AND MILLING TOOL

BACKGROUND OF THE INVENTION

Field of the Invention

The present invention relates to an indexable cutting insert for face milling with high feed rates, and to a milling tool for face milling with high feed rates, with a plurality of such indexable cutting inserts.

When machining in particular metallic materials by milling, it is customary to use milling tools which have a relatively tough carrier body which can be manufactured, for example, from tool steel to which a plurality of cutting inserts made of a harder, more wear-resistant material, in particular cemented-carbide, cermet or cutting ceramic, is fastened. The cutting inserts here have the cutting edges which enter into engagement in a machining manner with the workpiece to be machined. It is known in particular to design the cutting inserts as what as referred to as indexable cutting inserts which have a plurality of identical cutting edges useable in succession. The individual cutting edges are customarily indexed here by rotation of the respective cutting insert about one or more axes of symmetry (for example by 90°, 120°, 180°, 240°, 270° or other angles).

Different geometries are used here for the milling tools and the cutting inserts depending on the intended use. One use region is face milling with high feed rates, in which the milling operation is carried out at relatively low depths of cut, but at relatively high feed rates in the direction parallel to the workpiece surface to be machined.

In milling operations of this type, because of the high feed rate, relatively long cutting edge portions come into engagement with the workpiece to be machined, and it is important to provide as balanced as possible a distribution of the cutting forces at the cutting edge in order to achieve a long service life of the cutting insert.

JP S52-103081 A presents a miller with a carrier body which is equipped with a plurality of exchangeable cutting inserts which each have cutting edge portions which are convexly arched at least in sections.

Indexable cutting inserts composed of cemented carbide or cermet are customarily produced in a powder-metallurgical production process from starting powders which are mixed in accordance with the desired composition, are pressed in a mold into the desired shape and are subsequently sintered to form solid bodies. During the sintering of the pressed green compacts, compaction of the material occurs, which compaction is associated with shrinkage, wherein the uniformity of said shrinkage is greatly influenced by the geometry of the green compact and the pressure distribution achieved during the pressing. It has been shown that the service life which can be achieved for cutting inserts produced by powder-metallurgy greatly depends on the successful control of the powder-metallurgical production process.

BRIEF SUMMARY OF THE INVENTION

It is the object of the present invention to provide an improved indexable cutting insert for face milling with high feed rates, and an improved milling tool for face milling with high feed rates, with which cutting insert and milling tool a reliable milling operation and a long service life are made possible for indexable cutting inserts produced by powder-metallurgy.

The object is achieved by an indexable cutting insert for face milling with high feed rates as claimed. Advantageous developments are specified in the dependent claims.

The indexable cutting insert for face milling at high feed rates has an upper side, a lower side which has a smaller outer circumference than the upper side, and side surfaces connecting the upper side and the lower side. At the transition between the side surfaces and the upper side, rounded cutting corners are formed, which cutting corners are connected via convexly arched cutting edges which each run in a convexly curved manner from one cutting corner to an adjacent cutting corner. Adjacent to the cutting edges, the side surfaces each have main flanks which extend along the respective cutting edge in a continuously convexly curved manner from one cutting corner to an adjacent cutting corner. The main flanks extend in the direction of the lower side only over part of the height of the side surfaces and merge in a stepped manner into secondary surfaces which are set back inward.

By means of the continuously convexly curved profile of the cutting edges, a particularly balanced distribution of the cutting forces is achieved during milling with high feed rates. In combination with the main flanks which extend only over part of the height of the side surfaces and merge via a step into secondary surfaces which are set back inward, a particularly homogeneous pressure distribution during the pressing is made possible during the powder-metallurgical production process. The homogeneous pressure distribution results in a highly uniform distortion behavior during the sintering process, and therefore, after passing through the production process, the indexable cutting insert achieves a high service life for face milling with high feed rates.

According to a development, the cutting insert has a basic shape which is substantially quadratic in a top view of the upper side, with four cutting corners and four cutting edges connecting the cutting corners. In this case, a robust configuration of the cutting insert and at the same time a relatively large number of cutting edges which are useable individually are achieved.

According to a development, the main flank extends in the direction of the lower side over less than 50% of the height of the side surface, preferably over less than 40% of the height of the side surface. The effect achieved in this case is that the pressure distribution during the pressing and the distortion due to sintering can be very precisely controlled, and therefore a high service life is made possible. Furthermore, low flank wear is achieved in this case.

According to a development, the cutting edges have a profile substantially in the shape of a segment of an ellipse. A particularly balanced distribution of the cutting forces over the cutting edge is achieved in this case.

A bevel is preferably formed along the cutting edges and cutting corners on the upper side. In this case, the stability of the cutting edge is additionally increased by the bevel. The bevel preferably has a width of between 0.1 mm and 0.4 mm.

According to a development, the bevel runs in the region of the cutting corner at a first bevel angle within the range of between −10° and −20° with respect to a main direction of extent of the lower side and in the region of the center of the cutting edge at a more shallow second bevel angle of between 0° and −10°. The stated bevel angle is determined here between the bevel and the main direction of extent of the lower side, wherein a positive value for the bevel angle corresponds to a bevel declining toward the center of the cutting insert and a negative value corresponds to a bevel declining outward. The special indicated profile of the bevel achieves particularly great stability of the cutting edge at different machining parameters. The bevel therefore declines relatively sharply outward in the region of the cutting edge, as a result of which the cutting edge is particularly reinforced, and the bevel declines less sharply outward toward the center of the cutting edge or even assumes a neutral orientation. In this manner, a particularly advantageous distribution of the cutting forces and great stability of the cutting insert are made possible. According to a development, a region of the cutting edge that is adjacent to the cutting corner is designed as a transition region in which the angle of the bevel merges from the first bevel angle into the second bevel angle.

According to a development, the side surfaces are formed over their entire height at a cutting-insert-specific clearance angle of ≥0°.

The "cutting-insert-specific clearance angle" is understood here as meaning the clearance angle which is determined from the geometry of the cutting insert itself. It should be noted that the effective clearance angle resulting during the machining is additionally also determined by the installation position of the cutting insert on the cutting insert mount of the milling tool. The configuration of the cutting-insert-specific clearance angle in such a manner that the latter is not smaller than 0° over the entire height of the cutting insert permits particularly simple and reliable production of the cutting insert in a powder-metallurgical production process, in which a homogeneous pressure distribution during the pressing can be reliably achieved.

According to a refinement, the lower side is designed as a flat bearing surface. In this case, particularly reliable support and precise orientation of the cutting insert are made possible during operation.

According to a preferred development, at least part of the secondary surfaces is designed at least in regions as flat bearing surfaces. In this case, particularly stable and reliable positioning of the cutting insert is made possible.

According to a preferred refinement, the cutting insert has a through-hole which penetrates the cutting insert from the upper side to the lower side and is intended for receiving a fastening screw.

In particular in the case of a cutting insert which is manufactured in a powder-metallurgical production process, the features according to the invention have a very positive effect on the service life which can be achieved.

According to a development, the upper side can be provided with at least one chip geometry. For example, a chip geometry extending substantially over the entire profile of the cutting edge can be provided here, or, for example, respective chip geometries can also be provided in different regions of the upper side. The chip geometries can each have one or more depressions and/or one or more projections which direct, deform and/or break the chip formed during the machining.

The object is furthermore achieved by a milling tool for face milling with high feed rates as claimed in claim 15.

The milling tool has a holder with a plurality of cutting insert mounts, and a plurality of cutting inserts fastened to the cutting insert mounts of the type specified previously.

Further advantages and developments emerge from the description below of an exemplary embodiment with reference to the attached drawings.

DESCRIPTION OF THE INVENTION

An embodiment is described in more detail below with reference to the figures. First of all, an indexable cutting insert 1 is described in more detail with reference to FIG. 1 to FIG. 8.

The indexable cutting insert 1 is designed for face milling with high feed rates and is produced in a powder-metallurgical production process from appropriate starting powders. The cutting insert 1 is manufactured here in particular from cemented carbide or cermet, preferably from cemented carbide. Cemented carbide and cermet are materials in which hard particles are embedded in a binder matrix made from a more ductile material. In the case of cemented carbide, the binder matrix here can in particular substantially have cobalt (Co) or can be formed by cobalt and the hard particles can have in particular tungsten carbide (WC) and optionally, in smaller quantities, for example cubic carbides from groups 4, 5 or 6 of the periodic system of the elements. However, other binder components and/or hard particles are also possible.

The indexable cutting insert 1 according to the embodiment has an upper side 2, a substantially flat lower side 3 designed as a supporting surface, and a plurality of side surfaces 4 extending between the upper side 2 and the lower side 3. In a top view of the upper side 2, the cutting insert 1 has a substantially quadratic basic shape with rounded corners and convexly arched sides, as can be seen in particular in FIG. 3. The cutting insert 1 according to the embodiment is designed as what is referred to as a single-side cutting insert, in which cutting edges 5 and cutting corners 6 are formed only at the transition between the side surfaces 4 and the upper side 2. The lower side 3 of the cutting insert 1 furthermore has a smaller outer circumference than the upper side 2, and therefore the cutting insert 1 has what is referred to as a "positive" shaping, wherein the reference "positive" can be attributed to the cutting-insert-specific clearance angles realized.

The cutting corners 6 are of rounded design and have, as viewed in a top view of the upper side 2, a configuration in the shape of a segment of a circle with a predetermined radius. The cutting edges 5 each extend from a cutting corner 6 to an adjacent cutting corner 6 between the cutting corners 6. As viewed in the top view of the upper side 2, the cutting edges 5 each have, over the entire extent, a curved, convexly arched profile which is free from rectilinear portions. In the specifically illustrated embodiment, the cutting edges 5 have a particularly preferred profile which is in the shape of a segment of an ellipse and in which the respective cutting edge 5 extends along the contour of a segment of an ellipse. However, shapes differing from this specific shaping are also possible.

The indexable cutting insert 1 according to the embodiment therefore has four identically formed cutting edges 5 and four identically formed cutting corners 6. A through-hole 7 penetrates the cutting insert 1 from the upper side 2 to the lower side 3 and runs coaxially with respect to an axis of symmetry Z. The through-hole 7 is designed to receive a fastening screw, with which the cutting insert 1 can be fastened to a cutting insert mount 21 of a holder 20 of a milling tool 100, as will be described in more detail. The cutting insert 1 has four-fold rotational symmetry with respect to the axis of symmetry Z, and therefore the cutting insert 1 can be transferred into the same shape by rotation through 90°, 180°, 270° and 360° about the axis of symmetry Z. For indexing of the cutting insert 1 following wear of a first of the cutting edges 5, the next cutting edge 5 can therefore be brought into an active cutting position by rotation of the cutting insert 1 about the axis of symmetry Z.

The upper side 2 of the cutting insert 1 is designed, at least in the regions adjacent to the cutting edges 5 and cutting corners 6, as a rake face on which the chips from the machined workpiece that are formed during the milling are removed. Although a substantially flat configuration of the upper side 2 is illustrated schematically in the figures, the upper side 2 can preferably be provided in a manner known per se with chip geometries, i.e. with depressions and elevations, which have a chip-directing, chip-forming and/or chip-breaking action. Different configurations of the chip geometries are possible depending on the material to be machined, these not being discussed in more detail below. The upper side 2 can be designed here in particular in such a manner that, in a region directly adjacent to a bevel 8 on the cutting edge 5 or cutting corner 6, said upper side first of all declines in the direction of the lower side 3, at an increasing distance from the cutting edge 5 or cutting corner 6, and, after traversing a chip floor in the direction of the axis of symmetry Z, rises again, forming a chip back.

Figure 1:
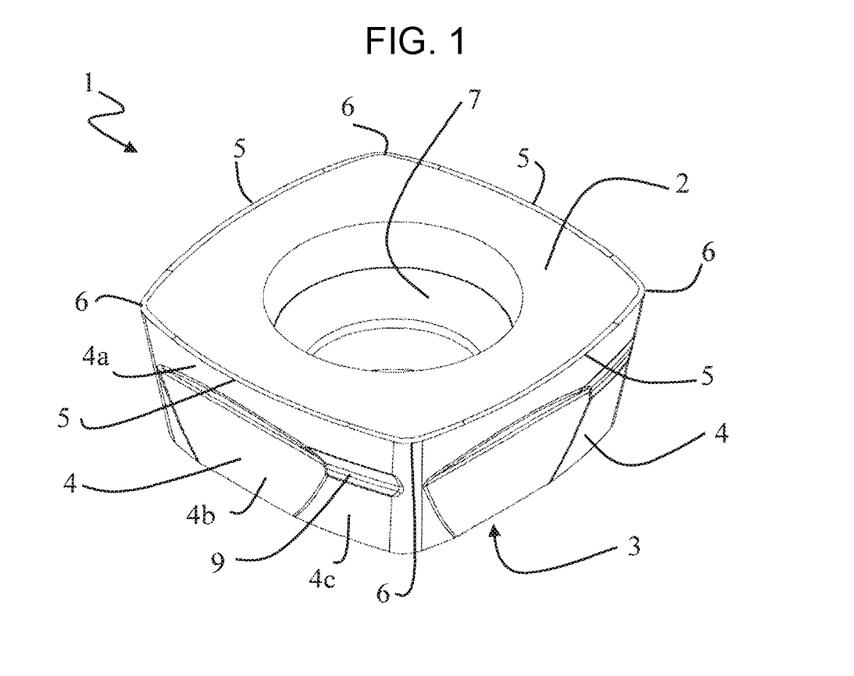
FIG. 1: shows a perspective illustration of an indexable cutting insert according to an embodiment.
Figure 2:
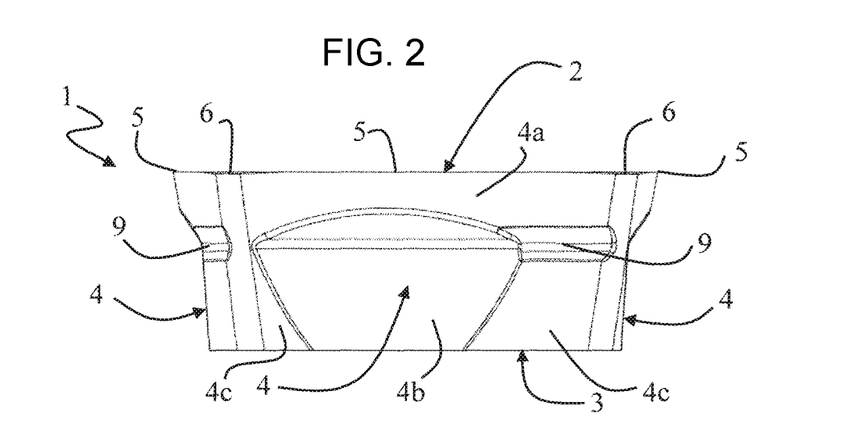
FIG. 2: shows a lateral illustration of the indexable cutting insert according to the embodiment.
Figure 3:
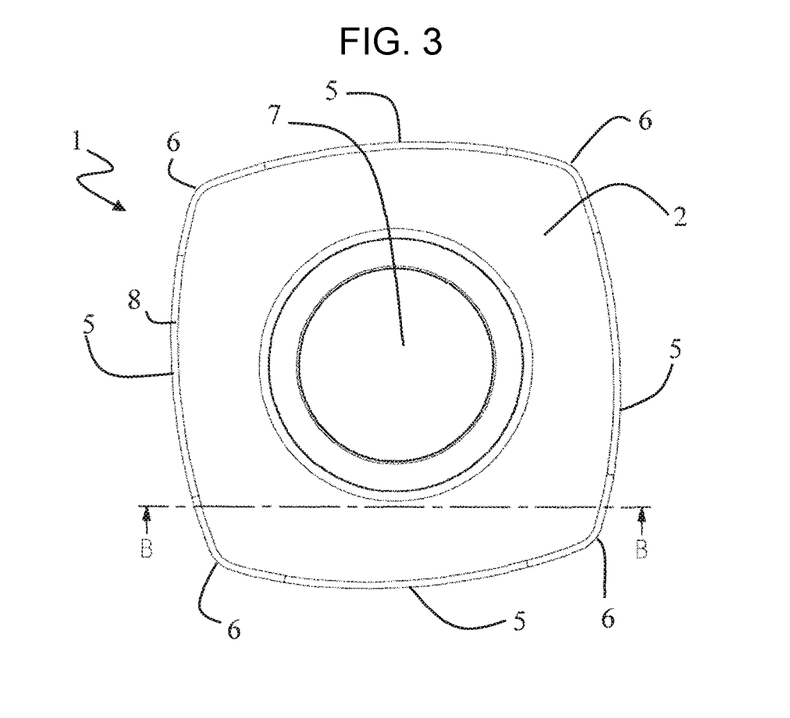
FIG. 3: shows a top view of the indexable cutting insert according to the embodiment.
Figure 4:
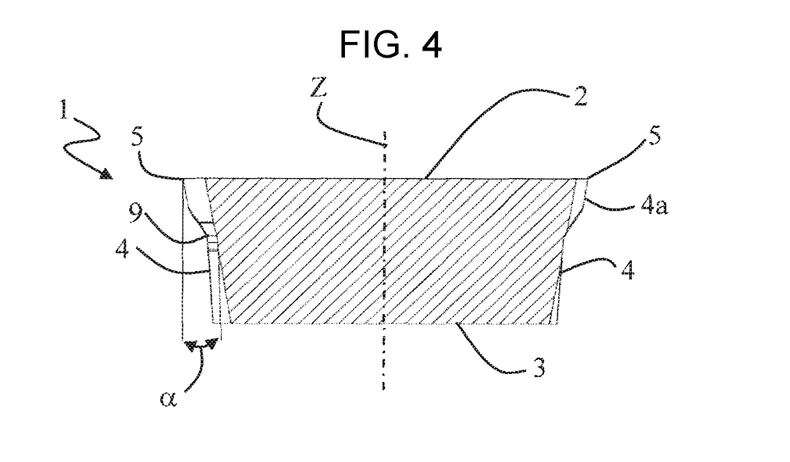
FIG. 4: shows a sectional illustration along the line B-B from FIG. 3.
Figure 5:
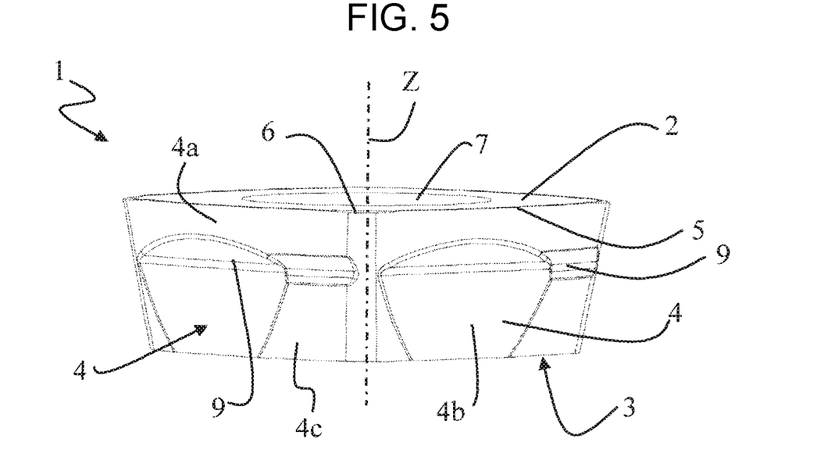
FIG. 5: shows a further perspective illustration of the indexable cutting insert according to the embodiment.
Figure 6:
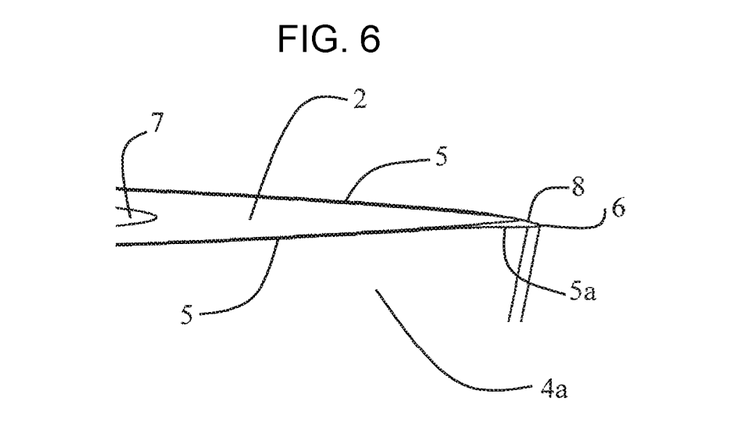
FIG. 6: shows an enlarged illustration of a detail of the upper right region of FIG. 5.
Figure 7:
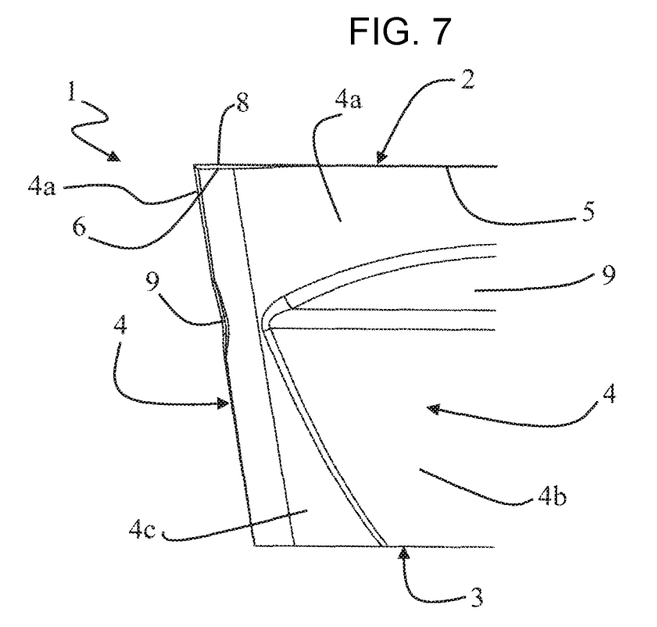
FIG. 7: shows an enlarged illustration of part of the indexable cutting insert in the region of a cutting corner.
Figure 8:
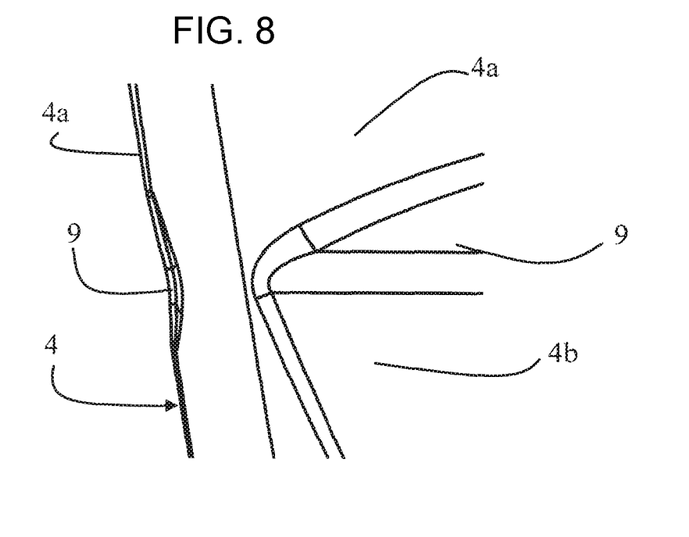
FIG. 8: shows a further enlarged detailed illustration of FIG. 7.

Along the cutting edges 5 and the cutting corners 6, the cutting insert 1 is provided with an encircling bevel 8 reinforcing the cutting edges 5 and cutting corners 6. The bevel 8 here preferably has a width in the direction perpendicularly to the cutting edge 5 or cutting corner 6 of between 0.1 mm and 0.4 mm. As can be seen in particular in FIG. 6, the bevel 8 is formed here in the region of the cutting corner 6 in such a manner that it declines outwards (i.e. at an increasing distance from the center of the cutting insert 1). The bevel 8 runs here in the region of the cutting corners 6 at a substantially constant first bevel angle within the range of between −10° and −20°, for example −15°. As can be seen in FIG. 6 and FIG. 2, the bevel runs at a more shallow second bevel angle, which is between 0° and −10°, for example 0°, in the embodiment, in the region of the cutting edges 5. As can be seen in FIG. 6, in a transition portion 5a of the cutting edge 5 directly adjacent to the cutting corner 6, the angle of the bevel 8 merges continuously from the first bevel angle into the more shallow second bevel angle. The transition portion 5a is relatively short and preferably has a length which corresponds to the cutting corner 6 in the region of 1.0 times to 1.8 times the radius of curvature. In the remaining region of the cutting edge 5, the bevel 8 has the more shallow second bevel angle preferably substantially constantly.

In the region directly adjacent to the cutting edges 5, the side surfaces 4 are designed as main flanks 4a which extend in a continuously convexly curved manner from one cutting corner 6 along the respective cutting edge 5 to the adjacent cutting corning 6. The main flanks 4a do not extend here over the entire height of the side surfaces 4 in the direction of the lower side 3, but rather only over part of the height of the side surfaces 4, preferably over less than 50% of the height of the side surfaces 4, more preferably over less than 40% of the height of the side surfaces 4.

In the direction of the lower side 3, the main flanks 4a merge in a stepped manner in the form of a step 9 recessed with respect to the center of the cutting insert 1 into secondary surfaces 4b and 4c which are setback inward. The side surfaces 4 of the cutting insert 1 have a smaller outer circumference over the entire height of the secondary surfaces 4b and 4c than in the region of the main flanks 4a. The side surfaces 4 are preferably designed here in such a manner that the side surfaces 4 overall, i.e. over their entire height and length, have a cutting-insert-specific clearance angle $\alpha$, for which $\alpha \geq 0$. In other words, the side surfaces 4 each run in an inwardly inclined manner in all regions in the direction of the lower side 3 or run parallel, at most in sections, to the axis of symmetry Z, and therefore the side surfaces 4 are formed free from undercuts. An undercut is therefore not formed in the region of the recessed step 9 either.

By means of the described configuration of the side surfaces 4 with the step 9 forming a recess, a homogeneous pressure distribution is achieved in the pressing operation during the powder-metallurgical production of the indexable cutting insert 1 according to the embodiment. This in turn results in readily controllable shrinkage behavior during the subsequent sintering of the pressed green compact, and therefore particularly good stability of the cutting edges 5 and of the main flanks 4a is achieved.

In the embodiment, the side surfaces 4 each have a first secondary surface 4b which is designed as a bearing surface for positioning the cutting insert 1 in a cutting insert mount of a milling tool. The first secondary surface 4b is of at least substantially flat design here. The side surfaces 4 furthermore have further secondary surfaces 4c with a convexly curved shape. In the region of the cutting edges 6, the side surfaces 4 each extend in a curved manner as far the transition between the side surfaces 4 and the lower side 3.

Figure 9:
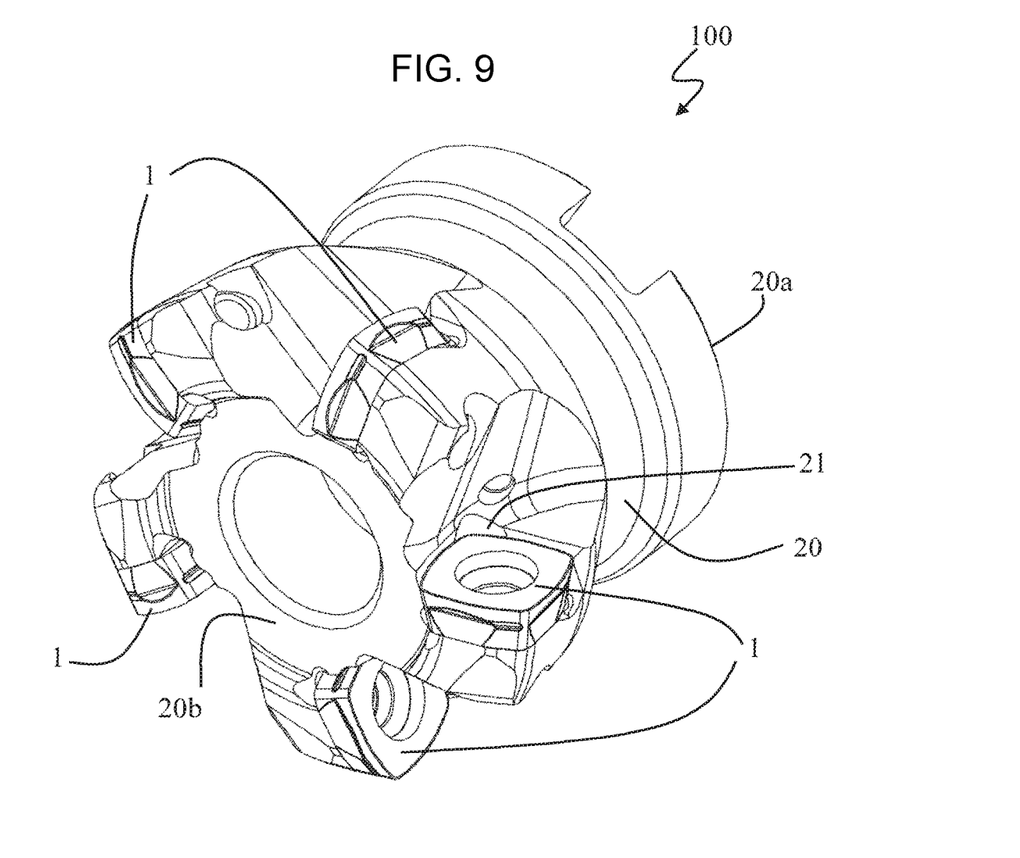
FIG. 9: shows a perspective illustration of a milling tool for face milling with high feed rates according to the embodiment.

FIG. 9 schematically illustrates a milling tool 100 with a plurality of the previously described indexable cutting inserts 1. Although FIG. 9 shows by way of example a milling tool 100 having a total of five such indexable cutting inserts 1, realizations are also possible in which the milling tool has fewer cutting inserts 1 or more cutting inserts 1.

The milling tool 100 is designed for face milling with high feed rates and has a holder 20, the one end 20a of which is designed for connection to a drive shaft of a milling machine. The milling tool 100 is designed to be driven in a rotating movement about an axis of rotation. A plurality of cutting insert mounts 21 for receiving one previously described indexable cutting insert 1 each are formed at the free end 20b of the holder 20. The cutting insert mounts 21 each have a main supporting surface for supporting the lower side 3 of the cutting insert 1, and at least one side supporting surface, preferably two side supporting surfaces, for supporting the first secondary surfaces 4b of the cutting insert 1, which secondary surfaces serve as bearing surfaces. A threaded bore for receiving a threaded portion of a fastening screw guided through the through-hole 7 in the cutting insert 1 is formed here in the main supporting surface.

The cutting insert mounts 21 are designed here in such a manner that the cutting inserts 1 fastened in the latter protrude from the holder 20 both in the axial direction and in the radial direction. The orientation of the main supporting surfaces and side supporting surfaces of the cutting insert mounts 21 determines the effectively realized rake angle and clearance angle during the milling operation. In the illustrated embodiment, the cutting insert mounts 21 are arranged distributed uniformly over the outer circumference of the holder 20 and each have corresponding orientations of the main supporting surfaces and side bearing surfaces.

The respective cutting insert mount 21 is designed here in such a manner that an indexable cutting insert 1 which is fastened therein and has a cutting edge 5, which can be referred to as the active cutting edge, protrudes over the holder 20 in the axial direction. Said active cutting edge 5 is oriented here in such a manner that an angle between the cutting edge 5 and a plane perpendicular to the axis of rotation of the milling tool 100 increases outward in the radial direction along the cutting edge 5. A radially inner region of the cutting edge 5 is oriented substantially perpendicularly to the axis of rotation of the milling tool 100.

The invention claimed is:

1. An indexable cutting insert, comprising:
an upper side having an outer circumference;
a lower side having a lower circumference smaller than the outer circumference of said upper side;
side surfaces connecting said upper side and said lower side, said side surfaces having a given height;
rounded cutting corners and convexly arched cutting edges formed at a transition between said side surfaces and said upper side, said cutting edges connecting said cutting corners to one another and said cutting edges each running in a convexly curved course from one said cutting corner to an adjacent said cutting corner;
said side surfaces having a main flanks adjacent said cutting edges, said main flanks each extending along a respective said cutting edge continuously convexly curved from one said cutting corner to an adjacent said cutting corner; and
said main flanks extending in a direction towards said lower side only over part of the given height of said side surfaces and merging in a stepped manner into secondary surfaces that are set back inward relative to said main flanks.

2. The indexable cutting insert according to claim 1, configured with a substantially square basic shape in a top view of said upper side, and wherein said cutting corners are exactly four cutting corners and said cutting edges are exactly four cutting edges connecting said four cutting corners.

3. The indexable cutting insert according to claim 1, wherein said main flanks extends in the direction of said lower side over less than 50% of the given height of the side surface.

4. The indexable cutting insert according to claim 3, wherein said main flanks extends in the direction of said lower side over less than 40% of the given height of the side surface.

5. The indexable cutting insert according to claim 1, wherein said cutting edges have a profile substantially in a shape of a segment of an ellipse.

6. The indexable cutting insert according to claim 1, which comprises a bevel formed along said cutting edges and said cutting corners on said upper side.

7. The indexable cutting insert according to claim 6, wherein said bevel has a width between 0.1 mm and 0.4 mm.

8. The indexable cutting insert according to claim 6, wherein said bevel runs in a region of said cutting corner at a first bevel angle within a range of between −10° and −20° with respect to a main direction of extent of said lower side and in a region of a center of said cutting edge at a larger second bevel angle of between 0° and −10°.

9. The indexable cutting insert according to claim 8, wherein a region of said cutting edge adjacent said cutting corner is a transition region in which the angle of said bevel merges from the first bevel angle into the second bevel angle.

10. The indexable cutting insert according to claim 1, wherein said side surfaces are formed over an entire height thereof at a cutting-insert-specific clearance angle of ≥0°.

11. The indexable cutting insert according to claim 1, wherein said lower side is a flat supporting surface.

12. The indexable cutting insert according to claim 1, wherein at least part of said secondary surfaces are flat bearing surfaces, at least in regions thereof.

13. The indexable cutting insert according to claim 1, formed with a through hole extending through the cutting insert from said upper side to said lower side and configured for receiving a fastening screw.

14. The indexable cutting insert according to claim 1, comprising a solid cutting insert body manufactured in a powder-metallurgical production process.

15. The indexable cutting insert according to claim 1, wherein said upper side is formed with at least one chip guiding feature.

16. A milling tool for face milling with high feed rates, comprising:
a holder with a plurality of cutting insert mounts; and
a plurality of cutting inserts, each according to claim 1 and each fastened to a respective said cutting insert mounts.

* * * * *